(12) United States Patent
Keitel et al.

(10) Patent No.: US 8,355,802 B2
(45) Date of Patent: Jan. 15, 2013

(54) SELECTIVE PARYLENE COATING FOR CARDIAC PACEMAKER ELECTRODES

(75) Inventors: Oliver Keitel, Aschaffenburg (DE); Frank Krüger, Nidderau (DE); Michael Pönitz, Hanau (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 882 days.

(21) Appl. No.: 12/486,006

(22) Filed: Jun. 17, 2009

(65) Prior Publication Data

US 2009/0312825 A1 Dec. 17, 2009

(30) Foreign Application Priority Data

Jun. 17, 2008 (DE) .......................... 10 2008 028 410

(51) Int. Cl.
*A61N 1/05* (2006.01)
(52) U.S. Cl. ...................................................... 607/127
(58) Field of Classification Search ........... 607/115–131
See application file for complete search history.

(56) References Cited

U.S. PATENT DOCUMENTS

| | | | | |
|---|---|---|---|---|
| 4,291,245 | A * | 9/1981 | Nowlin et al. | 307/400 |
| 6,501,994 | B1 | 12/2002 | Janke et al. | |
| 6,526,321 | B1 | 2/2003 | Spehr | |
| 8,142,431 | B2 * | 3/2012 | Ducharme | 606/47 |
| 2008/0071338 | A1 | 3/2008 | Jiang et al. | |

FOREIGN PATENT DOCUMENTS

DE 10 2008 028 410 B4 12/2009

OTHER PUBLICATIONS

Response of May 6, 2009 to DE Office Action issued Mar. 11, 2009 from the German Patent Office.
Allowance Decision issued Nov. 9, 2010 in DE Application No. 10 2008 028 410.6-54.

* cited by examiner

*Primary Examiner* — Carl H Layno
*Assistant Examiner* — Luther Behringer
(74) *Attorney, Agent, or Firm* — Panitch Schwarze Belisario & Nadel LLP

(57) ABSTRACT

A stimulation electrode is produced having a porous film layer and being partially coated with an insulating parylene (polyparaxylylene) film, whose insulating film has a dielectric breakdown voltage of greater than 100 V. Parylene is deposited on the entire surface of a porous film coating and then partially removed again by plasma. After the partial removal of the parylene, this porous film still has a capacitance of greater than 15 mF/cm$^2$ in a physiological NaCl solution at a frequency of 0.1 Hz. For the stimulation electrode, the transition from the insulating film to the porous film is formed so that the film thickness of the parylene film decreases continuously. In this way, a stimulation electrode having a porous film layer and being partially coated with an insulating parylene film is provided, whose electrode on the non-insulating parylene film-coated surface has a capacitance of greater than 15 mF/cm$^2$ in a physiological NaCl solution at a frequency of 0.1 Hz and whose insulating film advantageously has a dielectric breakdown voltage of greater than 100 V.

9 Claims, 2 Drawing Sheets

SELECTIVE PARYLENE COATING FOR CARDIAC PACEMAKER ELECTRODES

BACKGROUND OF THE INVENTION

The present invention relates to stimulation electrodes whose porous layer is partially coated with an insulating film.

According to U.S. Pat. No. 6,501,994, parylene (polyparaxylylene) is a preferred coating material. For creating a partial coating, U.S. Pat. No. 6,501,994 teaches the application of masks and their later removal. Here, a problem in the removal of the resist is that the parylene film always bleeds during the removal of the mask, and therefore does not lead to reproducible partial coatings, or the porous film is damaged by the mask or its removal. Standing against an inverse procedure, namely a fall-surface coating with parylene and subsequent partial removal, is that when the parylene film is removed, the porous layer located underneath is usually damaged and the high capacity achieved with difficulty by way of the porous layer would be undone.

BRIEF SUMMARY OF THE INVENTION

An object of the present invention is to partially coat the porous film layer with parylene in a reproducible way, without affecting the capacitance. It is desired, in particular, to define the coating made from parylene precisely and to avoid bleeding of the coating.

To achieve this object, parylene is deposited over the full surface of the porous film and removed both in a defined area and to a defined film thickness, so that the underlying porous film is not significantly damaged. A gas-phase polymerization of parylene is suitable for achieving a uniform coating. A parylene coating made uniformly in this way can be removed, in turn, by a plasma method whose parameters are oriented to the film thickness, without significantly negatively affecting the underlying porous film. In the plasma treatment, the edges of the windows in the parylene film do not bleed. Therefore, according to the invention, a stimulation electrode is disclosed on whose porous coating an insulating parylene film is partially deposited, whose transition to the porous film with continuously decreasing film thickness of the parylene film is a distinguishing feature. This allows precisely defined windows in the parylene film and high reproducibility in the production of these stimulation electrodes. In particular, according to the invention it is allowed that:

the film thickness of the parylene film decreases continuously;

the electrode on the non-insulating parylene film-coated surface has a capacitance of more than 15 $\mu F/cm^2$ in physiological NaCl solution at a frequency of 0.1 Hz;

the insulating film has a dielectric breakdown voltage of >100 V; and the porous film is made from a biocompatible material, such as, for example, Ir, TiN, or Pt.

In contrast to the method in which viscous starting materials are deposited, the method for coating helical substrates with polymers of the parylene family (in particular, parylene N, C, D, F) offers various advantages. These include, in particular, the ability of pore-free and homogeneous coating of strongly structured substrate surfaces. Electrical components can also be adequately insulated for low parylene film thicknesses of 5 $\mu$m-10 $\mu$m.

The additional property of biocompatibility of parylene N, C, D, and F qualifies this polymer for use as an insulating coating of helical cardiac pacemaker electrodes.

Suitable coating apparatuses comprise essentially a coating chamber, an evaporation unit for evaporating the original material, and a heated pyrolysis section. The entire system is connected to a vacuum pump, in order to maintain a processing pressure of 5 to 10 Pa.

In the coating method, in particular, the original material provided as a dimer is evaporated at a temperature from 150° C. to 160° C. and pyrolyzed at 700° C. into its associated monomer components. In the coating chamber, the resulting monomer components are deposited on the substrate bodies and bond to form a thoroughly cross-linked polymer film. The deposition can be promoted by temperatures of <40° C. prevailing in the coating chamber.

For implementing a partial parylene coating on helical cardiac pacemaker electrodes, the already deposited coating is removed selectively by a plasma etching method. According to an embodiment of the invention, by plasma methods parylene is selectively etched on very fine structures and removed without leaving residue, whereby biocompatibility is in turn guaranteed. Suitable plasma apparatuses essentially comprise a closed reaction chamber connected to a vacuum pump and a gas supply for introducing processing gases. According to an embodiment of the invention, the plasma excitation is realized by a microwave generator. At a processing pressure of 40 Pa the parylene film is selectively removed in an oxygen plasma. The use of aggressive tetrafluoromethane/oxygen plasmas is ruled out, because these have proved to destroy a titanium-nitride coating on the electrodes.

For the process-specific over-etching of the parylene coating, the capacitance of titanium-nitride coatings negatively affects the use of oxygen plasmas to a small extent, so that small over-etching is justifiable.

Porous films are generally used in medical technology, especially in stimulation electrodes, in order to lower their impedance and thereby to increase the capacitance. Such films have a film thickness from 1 to 15 $\mu$m, especially 2 to 10 $\mu$m. Characteristic of porous films made of titanium nitride or platinum is a structure made from interlinked tetrahedrons, wherein the size of the tetrahedron and the film thickness mutually influence each other during the growth. At a film thickness of 2.5 $\mu$m, many tetrahedrons definitely reach an extent of 0.5 $\mu$m, while other tetrahedrons reach only approximately 0.05 to 0.1 $\mu$m. Herein lies the basis for the porosity of the film. Especially for platinum, only a few tetrahedrons preferably grow and, again, others do not.

Iridium films grow in columns, so that the film growth is columnar. While some columns remain at a length of few tenths of $\mu$m, other columns reach up to the surface. Columns with rather uniform widths can be achieved, but columns are also produced that widen greatly toward the surface. At a film thickness of 3 $\mu$m, the column width at the film surface can equal up to one $\mu$m. The different columns produce a compact, porous film system.

The parylene is deposited in a film thickness of 5 to 10 $\mu$m on these films. Parylene can be coated on the entire surface in an especially uniform way and therefore forms a gap-less formation of the porous substrate even for very thin films. The tight formation of the substrate formed in this way is important for the electrical properties. This tightness is achieved with parylene due to the uniform coating even with very thin films. The full-surface parylene coating is partially covered between two half shells, and the uncovered part is removed in a selective plasma process. For this purpose, the plasma process is set to the exact film thickness of the parylene film, in order to preserve the porous film, especially the TiN.

A partial removal of the film from the helical surfaces is thereby achieved, in that a mask is used on the parylene film.

This mask can comprise mechanical components or viscous covers, wherein only regions of the helix have contact with the plasma, and the parylene coating is removed from these regions.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
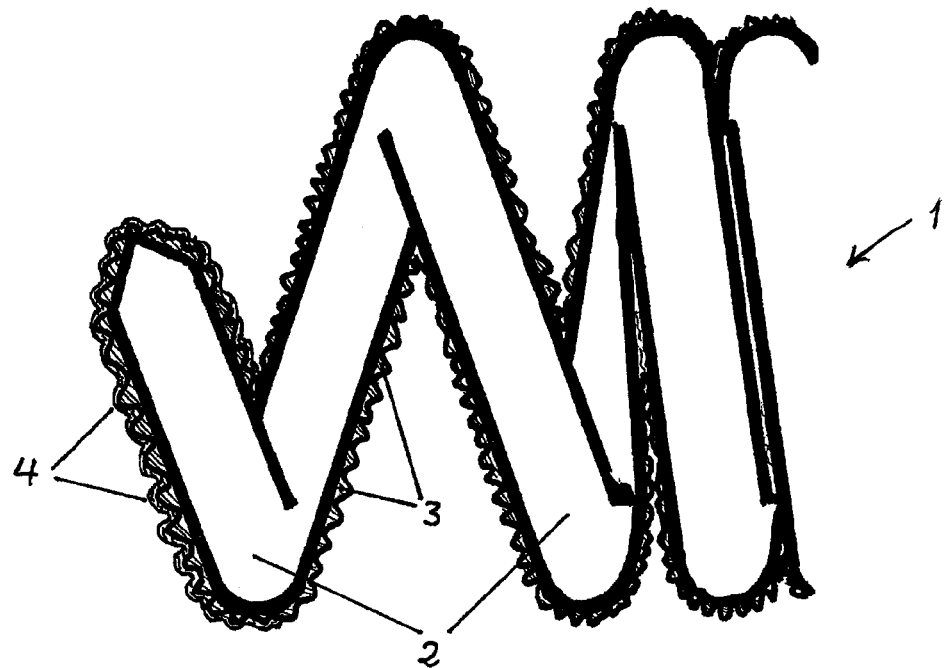
FIG. 1 is a schematic overall view of a stimulation electrode according to one embodiment of the invention in the form of a helix with coated and non-coated regions.
Figure 2:
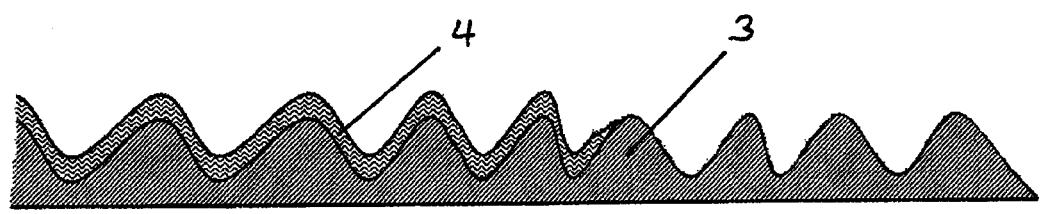
FIG. 2 is a sectional view of the transition from the insulated coating to the etched coating.
Figure 3:
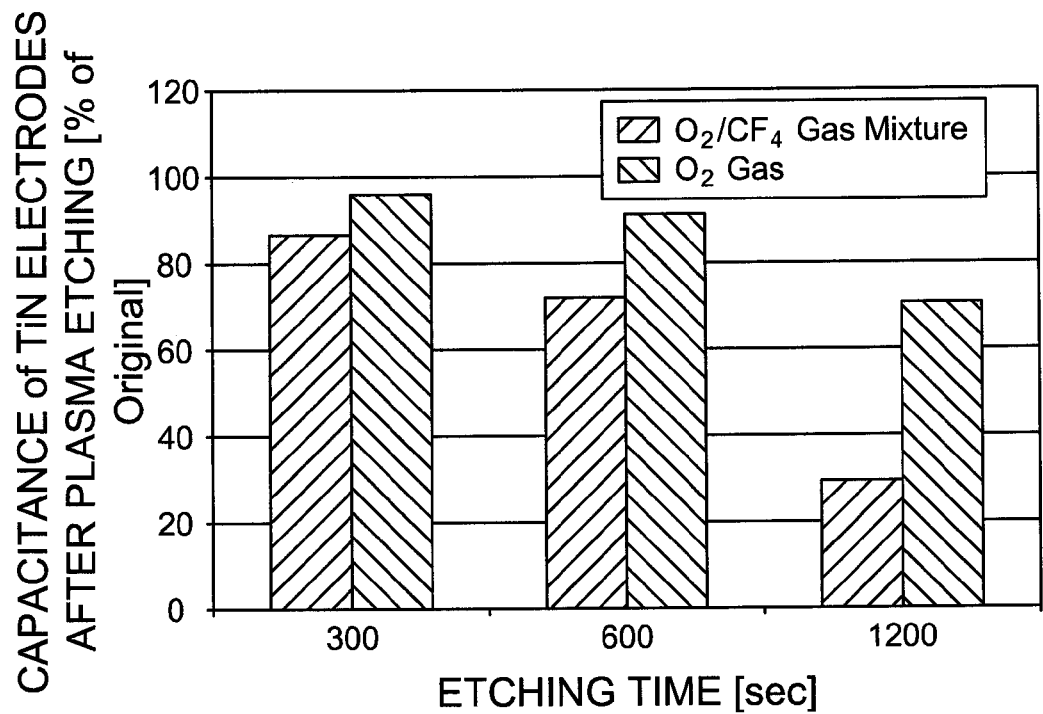
FIG. 3 is a bar graph showing the selectivity for etching with $O_2$.

For producing a stimulation electrode 1 according to FIG. 1, a porous coating 3 made from a biocompatible material according to U.S. Pat. No. 6,501,994 is deposited on an electrically conductive base body 2, especially a helix made from Pt or Pd. Here, the porous film 3 is coated completely and uniformly with a parylene film 4. For this purpose, an in-situ method is applied in which the parylene is deposited very uniformly on the porous film 3 due to in-situ polymerization.

The porous film 3 has a film thickness of 1-15 µm, especially 2-10 µm, and pores of, in particular, 3-8 µm, on which the parylene is deposited in a film thickness of 5-10 µm. The full-surface parylene coating 4 is masked between two half shells and is removed, where it is not masked, in a selective plasma process. For this purpose, the plasma process is set to the exact film thickness of the parylene film, in order to preserve the porous film, especially made from TiN.

The stimulation electrode produced in this way is then tested for its conductivity.

The parylene dimer available for the coating is evaporated in the vacuum system of the coating apparatus ("Labcoater" from the company PPCS) at a temperature of 150° C. to 180° C. and a pressure of 5 Pa. With a stepped increase of the temperature to 180° C., the entire original material does not evaporate instantaneously. Undesired intermediate reactions that degrade the insulation properties of parylene C are avoided for a slow temperature increase. After the evaporation phase, the gaseous dimer is then pyrolyzed at 700° C. into the associated monomer components and is deposited as a chained polymer in the deposition chamber. A layer thickness of 5-10 µm is sufficient for use as an insulator on pacemaker electrodes. A partial coating on these electrodes is not possible with this method, because any mask has minimal backing and leads to a strong formation of burrs during the removal after the coating process.

Achieving a Partial Coating

For implementing a partial coating 4 of parylene C on the electrodes 2 of a helical cardiac pacemaker 1, these are mechanically masked between two specially machined half shells and exposed to an oxygen plasma. The mask completely covers the regions of the helical electrodes 2 remaining insulated and exposes only the regions to be etched to the plasma. The substrates including the masks are exposed to the oxygen plasma at a pressure of 40 Pa. The plasma excitation is realized using a microwave generator with a power of 500 W. The processing gas is fed at a flowrate of 80 ml/min.

Because deposited parylene coatings 4 have small deviations in their film thicknesses due to unavoidable deviations within the coating process, continuing the process with the selective removal of film can compensate for these tolerances. That is, for a selective parylene removal, it is possible through this method to slightly over-etch already etched parts, without a sensitive TiN coating 3 located on the substrates becoming damaged to an unusable state.

For an average etching time of 1000 sec, an additional over-etching of 300 s to 600 s is possible. Here, parylene C itself is removed within the structures of the titanium nitrite 3.

Analogously, parylene N, D, and F can also be used. For the subsequent plasma treatment, in addition to the mask by means of two "half shells," other masks/fluids, etc., can also be used.

Figure 4:
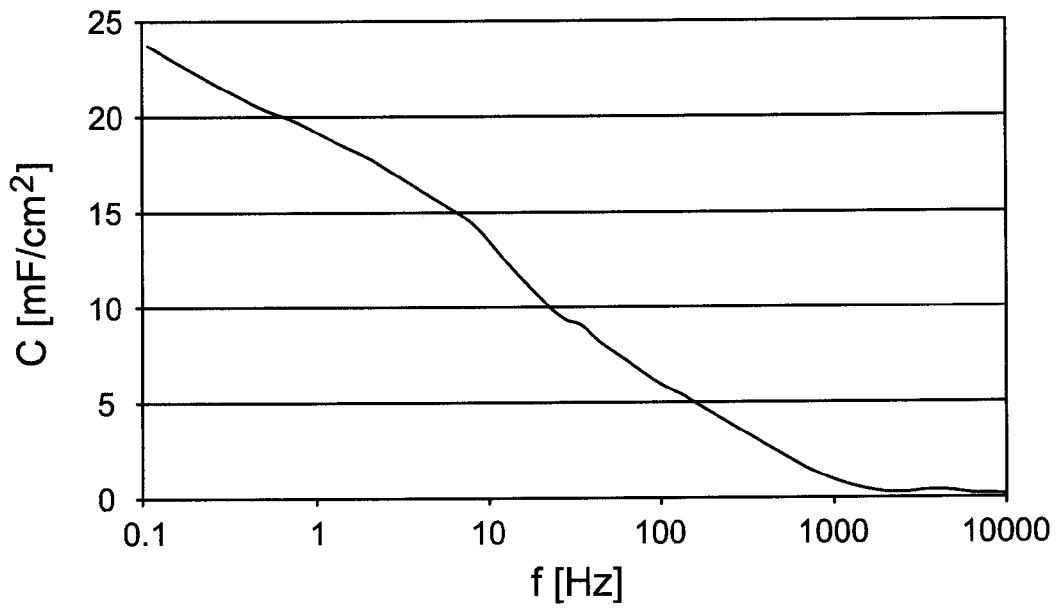
FIG. 4 is a linear graph showing the capacitance of the stimulation electrode produced according to the example.

FIG. 4 shows the specific capacitance [$mF/cm^2$] of a stimulation electrode according to the invention as a function of the frequency. At 0.1 Hz, greater than 15 $mF/cm^2$, in particular greater than 20 $mF/cm^2$, is achieved according to the invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A stimulation electrode comprising a porous film layer made of an electrically conductive biocompatible material and partially coated with an insulating film of parylene (polyparaxylylene), wherein a transition from the insulating parylene film to the porous film layer has a film thickness of the insulating parylene film which decreases continuously.

2. The stimulation electrode according to claim 1, wherein a surface of the stimulation electrode not coated with the insulating parylene film has a capacitance of greater than 15 $mF/cm^2$ measured in physiological NaCl solution at a frequency of 0.1 Hz.

3. The stimulation electrode according to claim 1, wherein the insulating parylene film has a dielectric breakdown voltage of greater than 100 V.

4. The stimulation electrode according to claim 2, wherein the insulating parylene film has a dielectric breakdown voltage of greater than 100 V.

5. The stimulation electrode according to claim 1, wherein the porous film layer comprises Ir or TiN or Pt.

6. A method for producing a stimulation electrode having a porous film layer and being partially coated with an insulating parylene (polyparaxylylene) film, wherein the insulating film has a dielectric breakdown voltage of greater than 100 V, the method comprising: depositing parylene over a full surface of the porous film layer and then partially removing the parylene deposit again by plasma, such that a transition from the insulating parylene film to the porous film layer has a film thickness of the insulating parylene film which decreases continuously, and such that after partially removing the parylene deposit, the porous film layer still has a capacitance of greater than 15 $mF/cm^2$ measured in a physiological NaCl solution at a frequency of 0.1 Hz.

7. The method according to claim 6, wherein the full-surface deposition of parylene is carried out by precipitation from a gas phase.

8. The method according to claim 6, wherein the partial removal of the parylene deposit is carried out by plasma etching.

9. The method according to claim 7, wherein the partial removal of the parylene deposit is carried out by plasma etching.

* * * * *